(12) United States Patent
Ravi

(10) Patent No.: US 8,877,227 B2
(45) Date of Patent: Nov. 4, 2014

(54) HYDROGEL NANOCOMPOSITES FOR INTRAOCULAR LENS APPLICATONS

(75) Inventor: Nathan Ravi, Chesterfield, MO (US)

(73) Assignee: The United States of America, as represented by the Department of Veterans Affairs, Washington, DC (US)

( * ) Notice: Subject to any disclaimer, the term of this patent is extended or adjusted under 35 U.S.C. 154(b) by 939 days.

(21) Appl. No.: 13/019,412

(22) Filed: Feb. 2, 2011

(65) Prior Publication Data

US 2011/0144228 A1      Jun. 16, 2011

Related U.S. Application Data

(60) Division of application No. 10/574,667, filed as application No. PCT/US2004/028637 on Sep. 3, 2004, now Pat. No. 8,153,156, which is a continuation-in-part of application No. 10/706,081, filed on Nov. 13, 2003, now Pat. No. 8,192,485.

(60) Provisional application No. 60/425,764, filed on Nov. 13, 2002, provisional application No. 60/499,887, filed on Sep. 4, 2003, provisional application No. 60/564,592, filed on Apr. 23, 2004.

(51) Int. Cl.
| | |
|---|---|
| *A61F 2/16* | (2006.01) |
| *A61L 27/50* | (2006.01) |
| *A61K 9/51* | (2006.01) |
| *A61L 27/52* | (2006.01) |
| *A61K 31/785* | (2006.01) |
| *A61K 9/00* | (2006.01) |

(52) U.S. Cl.
CPC ............. *A61K 9/0048* (2013.01); *A61L 27/50* (2013.01); *A61K 9/5138* (2013.01); *A61L 27/52* (2013.01); *A61K 9/5192* (2013.01); *A61K 31/785* (2013.01); *A61F 2/16* (2013.01)
USPC ........................................................ 424/427

(58) Field of Classification Search
CPC ..... A61F 9/0017; A61K 9/0051; G02B 1/041
See application file for complete search history.

(56) References Cited

PUBLICATIONS

Wang et al, "Controlled Structure and Properties of Thermoresponsive Nanoparticle-Hydrogel Composites", vol. 10, Issue 13, pp. 1074-1079, Jul. 2004.*
Zhao et al, "Thermoswitchable Electronic Properties of a Gold Nanoparticle/Hydrogel", vol. 26, Issue 22, pp. 1784-1787, Nov. 14, 2005.*
Ramaran et al, "Development of a Temperature-Sensitive Composite Hydrogel for Drug Delivery Applicastions", vol. 22, Issue 1, pp. 118-125, 2006.*

* cited by examiner

*Primary Examiner* — Carlos Azpuru
(74) *Attorney, Agent, or Firm* — Robert Gorman; Gorman Law Offices

(57) ABSTRACT

The present invention relates to reversible hydrogel systems. Particularly, the hydrogel of the present invention is made up of copolymers that can be a hydrogel when in an oxidized state and can be a solution when in a reduced state. A solution of the copolymer can be oxidized to form a hydrogel; and the hydrogel can be reduced to form a solution of the copolymer. Reversible nanogels can also be formed from a dilute solution of the copolymers. The hydrogel is formed with nanoparticles embedded therein to form a nanocomposite whose refractive index and modulus can be controlled by varying the amounts of nanoparticles and the polymer concentration of the hydrogel, respectively.

16 Claims, 12 Drawing Sheets a)

b)

HYDROGEL NANOCOMPOSITES FOR INTRAOCULAR LENS APPLICATONS

REFERENCE TO RELATED APPLICATIONS

This application is a divisional of pending U.S. patent application Ser. No. 10/574,667, filed on Apr. 5, 2007, which is a national stage filing of PCT Application No. 2004/028637 (WO 2005/023331), filed Sep. 3, 2004, which itself is a continuation-in-part of U.S. patent application Ser. No. 10/706,081, filed on Nov. 13, 2003, which in turn claims priority from U.S. Provisional Patent Application Ser. No. 60/425,764, filed on Nov. 13, 2002 as well as U.S. Provisional Patent Application Ser. No. 60/499,887, filed on Sep. 4, 2003, and 60/564,592, filed on Apr. 23, 2004, each of the above are all hereby respectively incorporated by reference.

FIELD OF THE INVENTION

The present invention relates to hydrogel systems that contain nanoparticles or nanophases. Particularly, the hydrogel of the present invention is made up of copolymers solution containing nanoparticles that can form a hydrogel triggered by changes in oxidation state, or light frequency and intensity, or mechanical stress. For example, a solution of the copolymer can be oxidized to form a hydrogel; and the hydrogel can be reduced to form a solution of the copolymer. One may also achieve reversibility using photo-addition chemistry, or using polymers that are sensitive to mechanical stress (physical gels that shear thin). The principles of the above technique may also be used to form reversible nanogels from a dilute solution of the copolymer. The hydrogel is formed with nanoparticles embedded therein to form a nanocomposite whose refractive index and modulus can be controlled by varying the amounts of nanoparticles and the polymer concentration of the hydrogel, respectively.

BACKGROUND OF THE INVENTION

A cataract is a cloudy or opaque area in the normally transparent crystalline lens of the eye. As the opacity increases, it prevents light rays from passing through the lens and focusing on the retina, the light sensitive tissue lining the back of the eye. Early lens changes or opacities may not disturb vision, but as the lens continues to change, several specific symptoms may develop including blurred vision, sensitivity to light and glare, increased nearsightedness, and/or distorted images in either eye.

There are no medications, eye drops, exercises, or glasses that will cause cataracts to disappear once they have formed. When a person is unable to see well enough to perform normal everyday activities, surgery is required to remove the cataract and restore normal vision.

In modern cataract extraction surgery, the cataract is removed from the lens through an opening in the lens capsule. Using an operating microscope, a small incision is made into the eye, and subsequently, the lens capsule. Microsurgical instruments are used to first fragment and then suction the cloudy lens from the eye. The back membrane of the lens (called the posterior capsule) is left in place. The focusing power of the optical system is then restored, usually only for distant vision, by replacement with a permanent pre-fabricated clear plastic intraocular lens (IOL) implant which became popular in the early 1980s.

Prior to the development of IOLs, cataract patients were forced to wear thick "coke bottle" glasses or contact lenses after surgery. Unfortunately, vision is not very good with thick eyeglasses and thick contact lenses do not provide a much better option. The discovery of IOLs solved this problem.

Intraocular lenses can be divided into two main groups: non-foldable and foldable. The original intraocular lenses were made from a hard plastic (non-foldable) material and could therefore be introduced into the eye only with an incision as large as the diameter of the lens. In order to reduce the trauma to the eye in cataract surgery, it is desirable to keep the incision through which the surgical procedure is conducted as small as possible. Foldable lenses are made of acrylic or silicone and can be rolled up and placed inside a tiny tube. The tube is inserted through a very small incision, less than 3.2 mm in length. Once inside the eye, the IOL gently unfolds.

Before the cataract surgery is performed, the corneal curvature and the axial length of the eye of the patient are measured to determine the proper focal power for the IOL that will be inserted. Using sophisticated formulas to calculate the corrective prescription power of the lens, the IOL not only replaces the need for thick glasses, but it can also correct the existing refractive error of the eye.

Although standard IOLs are available in a variety of focal lengths, those lengths are fixed for any given lens. Thus, unlike the natural lens of the eye, a standard IOL is unable to change focus. Therefore, the patient who must rely upon a standard IOL loses accommodative capability after surgery. IOLs are usually chosen that provide adequate distance vision. However, if distance vision is clear, then near vision may be blurred and the patient may require the use of reading glasses following cataract surgery.

Bifocal and multifocal IOLs have been developed to correct this problem. Although they are able to reduce or even eliminate the need for reading glasses, these IOLs produce a reduction in contrast sensitivity and the subjective experience of halos around lights.

A need exists, therefore, for a material that could mimic the natural lens of the eye and thus eliminate the need for reading glasses after cataract surgery. Such a material must be able to change its shape within the eye and thereby its refractive power. In addition to being used as an IOL in cataract surgery, such a material could also be used to treat other refractive errors including presbyopia (the physiologic loss of accommodation in the eyes due to advancing age).

Injectable, in situ forming gels have several potential uses in medicine, e.g., in intra-ocular lenses, as vitreous substitutes, and as drug delivery devices. In general, in situ forming gels have the advantage of being minimally invasive, easily deliverable, and able to fill native or potential cavities while conforming to different shapes, which may otherwise be difficult to prefabricate. The mechanism of gelation may be physical (changes in temperature, hydrogen bonding, hydrophobic interactions) or chemical (ionic or covalent bond formation). Usually, physical crosslinks are less stable than chemical ones. In situ gelation, resulting in networks covalently crosslinked through free-radical polymerization, may be initiated by heat, chemical initiators, or absorption of photons. Free-radical polymerization, however, is seldom quantitative: the resulting gel usually contains significant amounts of unreacted monomers, initiator, and accelerators-some or all of which may be toxic, and the reaction itself may be very exothermic. For ophthalmic applications in particular the requirements are stringent, and include a narrow range of reaction temperatures very close to ambient, optically clear material, very low chemical and photo-toxicity, and long-term stability in a wet, oxygenated, and photon-rich environment. The aim of the present invention in forming in situ gels is to develop new vitreous substitutes and injectable intraocular lens materials.

Accommodation is a dynamic process by which the refractive power of the optical system, principally the lens, is automatically adjusted to focus light on the retina. This ability is significantly decreased, usually by the fourth decade of life, and lost almost completely by the seventh decade of life through a progressive change in the volume and the elasticity of the lens resulting in an inability to focus on objects closer than arms length, a condition called presbyopia. Evacuating the capsular bag's contents and refilling it with an appropriate volume of a suitable material also offers a potential to restore accommodation to the presbyopic patient. Development of surgical procedures to evacuate the lens capsular bag through a small opening and identification of a suitable material to re-fill the capsular bag has been investigated. Such materials preferably have several advantages, including restoration of accommodation, a smaller corneosoleral incision than now required for semirigid replacement lenses, improved physiological positioning of the intraocular lens, and reduced rate of secondary opacification.

Both physical and chemical crosslinks for forming gels within the capsular bag have been exploited. For instance, Kessler (Experiments in refilling the lens. *Arch. Ophthalmol.* 71:412-417, 1964) used Carquille's immersion oil, silicone fluids, and damar gum to form physically crosslinked gels in rabbit eyes. Parel et al. popularized formation of gels by chemical crosslinking (Phaco-Ersatz: Cataract surgery designed to preserve accommodation. *Graefes Arch. Clin. Exp. Ophthalmol.* 224:165-173, 1986), which utilized filler-free divinylmethylcyclosiloxane elastomer that typically cured within several hours at room temperature. Nishi et al. (Accommodation amplitude after lens refilling with injectable silicone by sealing the capsule with a plug in primates. *Arch. Ophthalmol.* 116:1358-1361, 1998) used polymethyl-disiloxane containing hydrogen polysiloxane as a crosslinking agent. Others reported endocapsular polymerization in which a mixture containing monomers was injected and photopolymerized in situ to form the gel. Jacqueline et al. (Injectable intraocular lens materials based upon hydrogels, *Biomacromolecules* 2:628-634, 2001) recently reported the endocapsular photopolymerization of acrylate-modified N-vinylpyrolidone/vinylalcohol copolymer using an acrylamide-based photoinitiator, and identified some of the compositions to be dimensionally stable and optically clear. The toxicity, however, of unreacted monomers, and the exothermic nature of the polymerization reaction, makes the system impractical. Further, in all of the above cases, the mechanical properties of the refilling materials were not investigated. Neither were these chemically crosslinked gels reversible, thus making retrieval of the lens quite challenging.

In our previous work, we synthesized, characterized, and performed endocapsular polymerization with simultaneous gelation using polyethyleneglycol acrylates as a prototypic macromonomer. The extent of conversion during polymerization was approximately 95%, as is typical of most free-radical reactions. To address the issue of toxicity of the residual monomers, we quantitatively investigated the structure-toxicity relationship and observed that 1) acrylates were generally more toxic than methacrylates; 2) hydrophobic monomers were more toxic than hydrophilic ones in both classes; and 3) the mechanism of toxicity was probably from the ability of residual monomers to cross the lipid bilayer and subsequently react via Michael addition with intracellular proteins and DNA. We also observed that acrylate or methacrylates containing hydrophilic hydrogels were hydrolytically unstable in tissue culture medium. It is our continuing intention to identify and develop new techniques that will further our understanding of the use of polymers in ophthalmology, particularly as they influence accommodation and presbyopia.

It is, however, difficult to control the refractive index of a hydrogel without significantly changing the modulus of the material. Traditionally, the refractive index of a hydrogel can be changed by using different concentrations of the polymer; however, this results also in a change in the modulus of the material. Therefore, there remains a need for a substitute where the refractive index and modulus of the material can be controlled almost independently.

SUMMARY OF THE INVENTION

In an embodiment, the present invention provides reversible hydrogel systems of that are reversibly converted between a sol-gel phases by oxidation/reduction or by irradiation with different wavelengths of light or by application of shear as in the case of physical gels. The hydrogel can be reversed to form the solution; and the solution can be converted, by appropriate trigger, to form the hydrogel. Thus, the system is reversibly converted between a hydrogel and a solution.

The chemically reversible redox hydrogel system of the present invention includes a copolymer that is formed by polymerization of a monomer with a crosslinker. The crosslinker provides disulfide linkages within the copolymer molecule to form a hydrogel. When the hydrogel is reduced, the disulfide linkages are broken to yield a soluble copolymer solution. On the other hand, the copolymer solution can be oxidized (by oxygenation, disulphide interchange reaction, or photo-oxidation in presence of riboflavin and oxygen) to form disulfide linkages to reform the hydrogel. The oxidation is achievable at physiological pH of about 7.0 to about 7.4. The gels may also be formed by incorporating photosensitive groups that undergo 2+2 photoaddition or groups that photochemically react with thiols, such as thiol-acrylamides reactions. Hydrophobic hydrogels or associative hydrogels also exhibit such reversibility to shear forces, that is they will behave like a solution when a sheared and as a gel when the shearing force is removed or below a certain yield stress.

In another embodiment, the present invention provides a method of making nanogels (hydrogel nanoparticles) containing disulfide crosslinks. Preferably, the nanogels are made from reversible hydrogel systems that are reversibly converted between a hydrogel state and a solution by oxidation/reduction or by different wavelengths of light. The hydrogel can be reduced to form the solution; and the solution can be oxidized to form the hydrogel. Thus, the system is reversibly converted between a hydrogel and a solution. The nanogels are made by copolymerizing a monomer with a crosslinker to form a crosslinked hydrogel; reducing the crosslinked hydrogel to form a copolymer solution; diluting the copolymer solution to form a diluted copolymer solution; and subsequently oxidizing the diluted copolymer solution to form the nanogels. The thiol containing nanogels can also incorporate a metal particle, such as gold, therein. Additionally, all of the above concepts used in forming hydrogels can be potentially used to form nanogels by first diluting the copolymer solution to be its critical concentration.

In yet another embodiment, the present invention combines a reversible hydrogel with nanoparticles to form a hydrogel nanocomposite for use as an accommodating injectable intra-ocular lens. The inventive nanocomposite comprises nanoparticles dispersed in a polymer hydrogel formulation, and is advantageous in that the refractive index and modulus of the material can be controlled using two variables, namely the concentration of nanoparticles and the copolymer concentration in the hydrogel. The refractive index is controlled by changing the amount of nanoparticles; and the modulus can be controlled by changing the polymer concentration in the hydrogel. The nanoparticle preferably has a particle size less than about 150 nm, and most preferably about 3-20 nm, most importantly it has to be non-scattering. It is critical that the nanoparticles be of such dimensions that they do not disperse or scatter visible light. The nature of the nanoparticle is less critical and could be a nanogel, protein, silica, gold, silver, $TiO_2$, any transition metals, ceramic, or combinations thereof as long as it is dispersible in aqueous medium, does not scatter visible light, and remains stable with the polymer formulation.

DETAILED DESCRIPTION OF THE PREFERRED EMBODIMENTS

I. Reversible Hydrogel Systems

Figure 1:
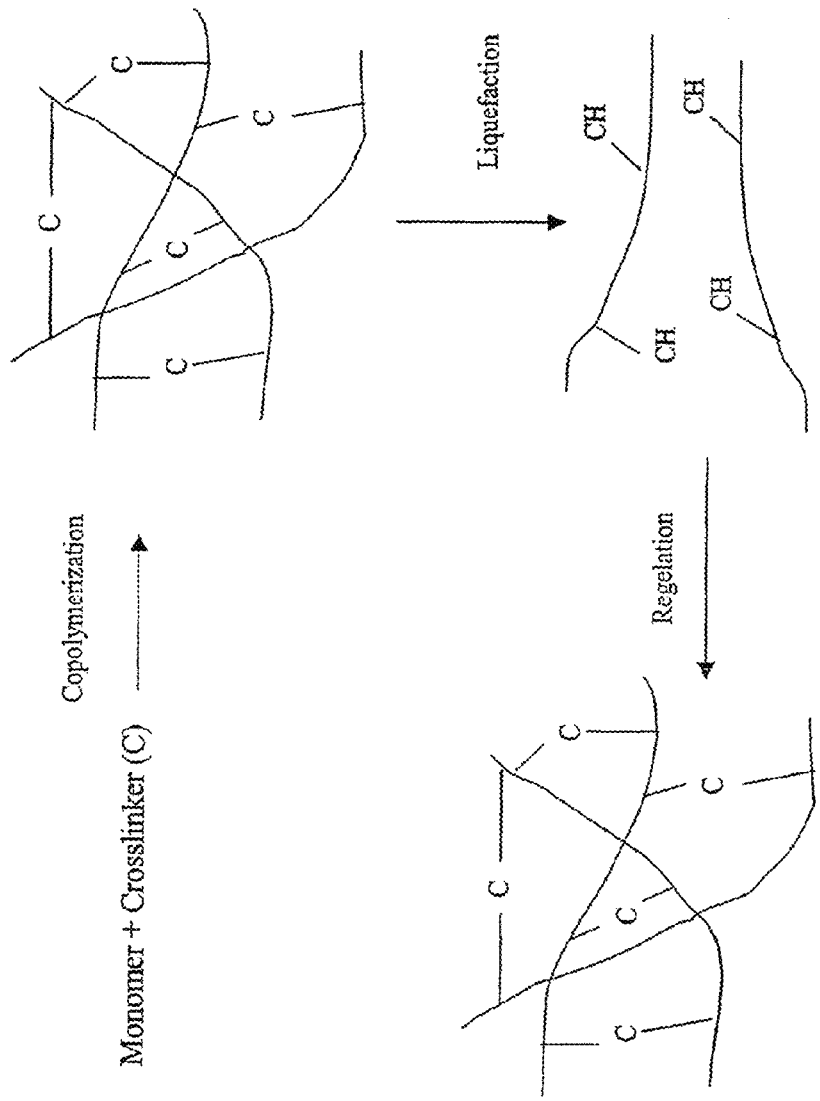
FIG. 1 shows the general process of the making the reversible hydrogel system.

The hydrogel systems of the present invention contains a copolymer that is a hydrogel in one state and is in a solution in another state. The copolymer is preferably obtained by copolymerizing a monomer with a crosslinker. The crosslinker provides intermolecular crosslinkages to form the hydrogel. The monomer can be acrylamide, N-ornithine acrylamide, N-(2-hydroxypropyl)acrylamide, hydroxy-ethylacrylate, hydroxyethylmethacrylate, N-vinyl pyrolidone, N-phenylacrylamide, dimethylaminopropyl methacrylamide, acrylic acid, benzylmethacrylamide, methylthioethylacrylamide, or combinations thereof. Macro-monomers or polymers with functional groups for example, polyethyleneglycol acrylates, polyethyleneglycol methacrylates, polyvinyl alcohol etc, that can be modified or derivatized to incorporate disulfide groups or reversible crosslinks may also be appropriate for the present invention. The preferred polymer system has a semiflexible or rigid water soluble polymer backbone, such as polyacrylic acids, polystyrene sulfonic acids; collagen; polysaccharides.

The polymer preferably includes crosslinkable groups which are capable of forming covalent bonds within the polymer or with other polymers while in aqueous solution, which permit crosslinking of the polymer to form a gel, either after, or independently from thermally or photochemically dependent gellation of the macromer. Chemically or ionically crosslinkable groups known in the art may be provided in the macromers. The preferred crosslinkable groups are unsaturated groups including vinyl groups, allyl groups, cinnamates, acrylates, diacrylates, oligoacrylates, methacrylates, dimethacrylates, oligomethoacrylates, acrylamides, or other biologically acceptable photopolymerizable groups. The crosslinker is preferably a disulfide linker, such as N,N'-bis (acryloyl)cystamine (BAC). Other useful crosslinkers include, but are not limited to, methylenebisacrylamide, methylenebismethacrylamide, esters of unsaturated mono- or polycarboxylic acids with polyols, such as diacrylate or triacrylate, e.g., butanediol diacrylate, butanediol dimethacrylate, ethylene glycol diacrylate, ethylene glycol dimethacrylate, and also trimethylolpropane triacrylate, allyl compounds, such as allyl (meth)acrylate, triallyl cyanurate, diallyl maleate, polyallyl esters, tetraallyloxyethane, triallylamine, tetraallylethylenediamine, pentaerythritol triallyl esters or allyl esters of phosphoric acid, and also vinyl compounds such as vinyl acrylate, divinyl adipate, divinylbenzene and vinylphosphonic acid derivatives. Other non-reversible linkers can be included in the polymer to form branches.

Photochemically reversible linkers appropriate for the present invention can include, but are not limited to, stilbene, azo, and cinnamoyl derivatives. Typically, with photochemically reversible linkers, gellation of the copolymer occurs at a particular wavelength, while liquefaction of the copolymer occurs at a different wave length. For example, the copolymer solution forms a hydrogel by exposure to a first wavelength; and the hydrogel reverts to a copolymer solution by exposure to a second wavelength.

FIG. 1 shows a schematic of the formation of the hydrogel, solubilization of the copolymer, and reformation of the hydrogel. The copolymerization of the monomer with the linker forms a crosslinked hydrogel. The polymerization is initiated with water-soluble or monomer-soluble initiators or redox initiator combinations. Examples of water-soluble initiators are the sodium, potassium and ammonium salts of peroxodisulfuric acid, hydrogen peroxide, tert-butyl peroxide, tert-butyl hydroperoxide, potassium peroxodiphosphate, tert-butyl peroxypivalate, cumyl hydroperoxide, isopropylbenzyl monohydroperoxide and azobisisobutyronitrile. Examples of monomer-soluble initiators are diacetyl peroxydicarbonate, dicyclohexyl peroxydicarbonate and dibenzoyl peroxide. The initiators are generally used in an amount of 0.01 to 0.5% by weight, based on the total weight of the monomers. Combinations of said initiators in combination with reducing agent(s) may be used as redox initiators. Suitable reducing agents can be, but are not limited to, the sulfites and bisulfites of alkali metals and of ammonium, for example, sodium sulfite, derivatives of sulfoxylic acid such as zinc or alkali metal formaldehyde sulfoxylates, for example sodium hydroxymethanesulfonate, and ascorbic acid. The amount of reducing agent is preferably 0.01 to 0.5% by weight, based on the total weight of the monomers.

Once the copolymer is formed, it is preferably washed to completely remove unreacted monomers and crosslinkers. The washing step is especially preferred for monomers that are toxic to human use. For example, acrylamide is a known carcinogen and neurotoxin; however, its polymer, polyacrylamide, is harmless. Thus, after polymerization of acrylamide, it is highly desirous that the unreacted acrylamide is completely washed from the hydrogel. After removal of unreacted monomers and crosslinkers, the copolymer can be further swollen by a liquid, preferably water, to obtain the desired water content.

The hydrogel can be liquefied to form a solution of the copolymer by disruption of the crosslinkages. In the case of disulfide linkages, liquefaction can be accomplished by chemically reducing the hydrogel so that the disulfide linkages are reduced to thiols. Reduction preferably takes place in the presence of a reducing agent, such as dithiolthreitol (DTT). Other reducing agents can be, but are not limited to, of 2-mercaptoethanol, dithioerythritol, cystein, butanethiol, sodium borohydride, cyanoborohydride, mercaptoethylamine, ethylmaleimide, and tri(2-carboxyethyl)phosphine hydrochloride (TCEP.HCl). The reducing agent is selected based on the nature of the crosslinkage. For disulfide linkages, DTT is the preferred reducing agent. Once reduced, the hydrogel liquefies and becomes a copolymer solution. In the case of copolymers having disulfide bonds, reduction results in the thiols containing copolymers that are water soluble.

The copolymer solution can be diluted, concentrated and/or dried as desired. For storage, the copolymer is preferably precipitated from solution, for example by methanol, filtered, and dried. Other methods, including freeze drying, are also appropriate. The stored copolymer solids can subsequently be dissolved in a solution to desired concentrations for use.

The hydrogel can be reformed from the copolymer solution by reforming the crosslinkages within the copolymer molecule. In the case of disulfide linkages, regelation can be accomplished by oxidization of the copolymer solution, preferably in the presence of an oxidizing agent, preferably atmospheric oxygen. Although atmospheric oxygen is preferred, other oxidizing agent, such as dithiodipropionic acid (DTDP), cystamine, 2-hydroxyethyldisulfide hydrogen peroxide, organic peracids, peroxy carbonates, ammonium sulfate peroxide, benzoyl peroxide, perborates, and the like, can also be used. Importantly, however, the preferred oxidizing agents should have no significant toxicity to human and/or animals.

With polymers using photochemically dependent linkers, such as stilbene, azo, cinnamoyl derivatives, regelation is accomplished by exposing the copolymer solution to light at an appropriate wavelength. Liquefaction of reversible groups can thus be accomplished by exposing the gel to light at an appropriate wavelength, usually one that is different from the gelation wavelength.

It is noted that both photochemically dependent linkers and oxidation dependent linkers are not exclusive. Both types of linkers can be used in the same polymer to achieve desired results. For example a polymer containing both types of linkers can be prepared and washed using oxidation/reduction; however, once a lens is formed, the photochemically dependent linker can also be activated to form a more permanent and stable hydrogel. In this embodiment, reversible linkers can be used along with non-reversible linkers. For example, the polymer can use a reversible oxidation/reduction reversible linker and a non-reversible photochemical dependent linker, such as thiol-acrylamide and/or thiol-acrylates.

II. Nanogels

The hydrogels above can also be used to make nanogels whose particle size depends on the molecular weight of the copolymer. The method of the present invention teaches the art of making nanogels having diameters of less than 150 nm, preferably about 3-20 nm, which exhibit refractive indexes similar to that of the natural lens. The chemistry involved in preparing reversible hydrogels in section I above are appropriate for making nanogels. The nanogels are made by copolymerizing a monomer with a crosslinker to form a crosslinked hydrogel; reducing or irradiating the crosslinked hydrogel to form a copolymer solution; diluting the copolymer solution to form a diluted copolymer solution; and oxidizing the diluted copolymer solution to form the nanogels. Thus, the process of making the nanogels is virtually identical to that of the reversible hydrogel, except that the nanogel is formed from a dilute copolymer solution. By dilute, it is meant that the concentration of the copolymer solution is less than 1 percent (w/v), preferably less than 0.5 percent (w/v), and most preferably less than 0.01 percent (w/v). Therefore, when the copolymer concentration is dilute, nanogels forms by the oxidation and/or irradiation of the copolymer solution; and when the copolymer concentration is concentrated, a hydrogel form by the oxidation and/or irradiation of the copolymer solution. The dilute copolymer solution minimizes intermolecular interaction, and thus, the crosslinkages are formed intramolecularly, which results in the formation of nanogels. On the other hand, when the copolymer solution is more concentrated, intermolecular crosslinkages dominate to form hydrogels.

In an embodiment of the present invention, the thiol containing nanogel particle can also encapsulate a metal particle, such as gold. In this case, metal particles, due to their propensity for thiol groups, react spontaneously. In the absence of metals, the solution is oxidized or irradiated to form intramolecular crosslinkages resulting in nanogels. However, during the formation of the nanogels, metal particles are trapped within the nanogels. If the concentration of metal particles is low enough, it is possible to achieve association of a single metal particle with a nanogel particle. Depending on the metal, crosslinkage can also occur between the metal particle and the nanogel. For example, gold can crosslink with —SH groups of the copolymer upon oxidation.

III. Hydrogel Nanocomposite

These hydrogel materials exhibit moduli similar to that of the natural lens; however, the refractive indexes of the hydrogel are usually less than that of natural lens material. Usually the refractive index scales linearly with polymer concentration while the modulus scales exponentially. Thus in an ideal hydrogel, it is almost impossible to have a material with high refractive index and low modulus. Applicant has discovered that a nanocomposite of the hydrogel and nanoparticles can achieve both high refractive index (RI) and low modulus, similar to those of the natural lens. The nanocomposite system also exhibits similar accommodation characteristics of the natural lens, preferably within about 1 second, more preferably within about 50-250 milliseconds.

The hydrogel nanocomposite of the present invention contains nanoparticles dispersed in a reversible hydrogel matrix, and is advantageous in that the refractive index and modulus of the material can be controlled by varying two variables, namely nanoparticle concentration in the hydrogel and copolymer concentration in the hydrogel. The RI is controlled by changing the nanoparticle concentration in the hydrogel; and the modulus can be controlled by changing the polymer concentration in the hydrogel. This is particularly true in the case of non-interacting nanoparticles. However, if the nanoparticles interact with the copolymer backbone then, depending on the crosslink density and particle size one may have a system in which the modulus increases with nanoparticles (or RI).

The nanoparticle preferably has a particle size less than about 150 nm, and most preferably about 3-20 nm. It is critical that the nanoparticles be of such dimensions that they do not disperse or scatter visible light. The nanoparticles can be, but is not limited to, polymeric nanogels (see section II above), proteins, silica, metals, such as gold, silver, and any transition metals, $TiO_2$, ceramics, or combinations thereof as long as it is dispersible in aqueous medium and remains stable with the polymer formulation, and preferably does not interact with the polymer backbone.

The reversible hydrogel previously described in section I makes the preferred matrix for the nanocomposite; however, other hydrogels are also appropriate for the present invention.

To make the nanocomposite, the nanoparticles are added to the liquefied copolymer solution and stirred to form a uniform dispersion. The dispersion is then oxidized and/or irradiated to form the nanocomposite of the present invention.

When nanogels are used as the nanoparticles, it is preferred that the nanogels and the reversible hydrogel contain different crosslinkable groups. For example, if the hydrogel uses oxidation/reduction linkers, the nanogels preferably use photochemical dependent linkers, and vice versa. More preferably, the nanogels contain both oxidation/reduction and photochemical dependent crosslinking groups to achieve greater stability and permanence.

In a preferred embodiment, the nanoparticle should be chosen so that crosslinking between the hydrogel matrix and the nanoparticles are minimized. In this case, if there is no crosslinking between the matrix and the nanoparticles, the RI and modulus of the nanocomposite can be controlled substantially independently. Particularly, the RI can be controlled by adjusting the concentration of nanoparticles in the hydrogel; and the modulus can be controlled by adjusting the copolymer concentration in the hydrogel. The higher the level of interaction and/or crosslinking between the hydrogel matrix and the nanoparticles, the lower the ability to independently control the RI and modulus of the nanocomposite.

To form a lens replacement, the nanocomposite should achieve a RI of about 1.40 to 1.41 and a modulus of about 1,000 to 1,500 Pascals.

Without further description, it is believed that one of ordinary skill in the art can, using the preceding description and the following illustrative examples, make and utilize the compounds of the present invention and practice the claimed methods. The following example is given to illustrate the present invention. It should be understood that the invention is not to be limited to the specific conditions or details described in this example.

Example 1

Acrylamide/BAC Hydrogels

Experimental Methods
Synthesis of Polyacrylamide/BAC Hydrogels

Varying compositions of hydrogels were synthesized by reacting acrylamide (Aam) with BAC at acrylic mole ratios of 98/2, 96/4, and 94/6 at 5% (w/w) in 25% ethanol (25:75=ethanol:water v/v). Nitrogen was bubbled through the solution for about 30 minutes to displace any dissolved oxygen prior to the initiation of the polymerization. The reaction was initiated by adding 2.1% (w/w) of TEMED and 0.4% (w/w) of APS and allowed to proceed for 15 hours at 25° C. Aqueous ethanol was used as solvent because of the limited solubility of BAC in water. The resulting gels were removed from the beaker, swelled in 500 mL of water for two days, crushed into small pieces, and washed with distilled water. The gels from the above copolymer compositions were labeled as ABSS2, ABSS4, and ABSS6, indicating that they contained disulfide (—SS—) bonds by incorporating 2, 4, and 6 acrylic mole % of BAC, respectively.

Reductive Liquefaction of Monomer-Free Swollen Hydrogels

The gels were crushed into small pieces and liquefied by adding DTT, at 10 mol/mol of BAC, at pH 7.0. Nitrogen was bubbled through the solution under stirring while the reduction was carried out for two, four, and six hours for ABSS2, ABSS4, and ABSS6, respectively. After the gels were completely dissolved, the solution was acidified to pH 3 using 10% (v/v) HCl and precipitated in excess methanol under vigorous stirring. The precipitated —SH polymer was filtered, dried under vacuum, and stored under reduced pressure until needed. The above soluble polymers from ABSS2, ABSS4, and ABSS6 were labeled as ABSH2, ABSH4, and ABSH6 respectively, indicating that they now contained —SH groups instead of disulfide bonds.

Characterization of the Soluble Copolymers

The thiol (—SH) content of each copolymer was determined using Ellman's reagent. Briefly, 50 µL of 0.5% (w/v) copolymer solution (pH 4, nitrogen bubbled) was added to a mixture of 50 µL of 0.01 M Ellman's reagent (in 0.1M phosphate buffer, pH 8.0), 500 µL of 0.1 M phosphate buffer (pH 8), and 450 µL of distilled water. Absorbance (using Beckman DU54 spectrophotometer) of the resulting solution at 412 nm was determined five minutes after mixing. The concentration of the —SH in each ABSH polymer was calculated using the molar absorptivity of 13,600 $M^{-1}$ $cm^{-1}$.

Molecular weights of the reduced polymers were determined using a Viscotek HPLC-GPC system (Houston, Tex.) equipped with static light scattering and refractive index detectors in tandem with a viscosity detector. The stationary phase consisted of a dual column of G6000PWXL and G4000PWXI. (Tosoh Biosep, Montgomeryville, Pa.), connected in series, and the mobile phase was 20 mM Bis-Tris buffer (pH 6.0, 0.1% sodium azide). Samples were prepared in water (pH 4, $N_2$ saturated) at a concentration of 0.5% (w/v). Polyethylene glycol standards (Viscotek, Houston, Tex.) of molecular weight (Mw) 1000 to 950,000 were used for calibration.

The presence of thiol groups in the soluble polymers and their disappearance on regelation was investigated by Raman spectroscopy (Kaiser Holoprobe Series 5000 Raman spectrophotometer, operating at the Argon laser wavelength of 514 nm). Aqueous polymer samples, in a vial, were directly exposed to the laser beam, and spectra were acquired at a resolution of 2 $cm^{-1}$. A custom-built sample holder was utilized on the commercially available translation stage to allow reproducible placement of samples with respect to laser focus. The spectra were analyzed using the GRAMS/32 software package (Galactic Industries Corporation, Salem, N.H.).

Regelation of copolymer solutions was performed using DTDP (details given below), after which the gel was swelled for two days. The swollen gel, after washing with water several times, was used for the Raman experiments to observe the disappearance of the peak for —SH moiety and the appearance of a peak corresponding to the formation of the disulfide (—S—S—) bonds.

Regelation of Copolymeric Aqueous Solution

Three different concentrations (% w/v) of polymer solutions, in nitrogen saturated water at pH 4, were prepared from each of the reduced polymers: 10.0, 12.5, and 15.0% from ABSH2; 5.0, 7.5, and 10.0% from ABSH4; and 2.0, 3.0, and 4.0% from ABSH6. Polymer solutions (1 mL each) were placed incest tubes and the pH of the solutions were adjusted to approximately 7.4 using calculated amounts of 10 M NaOH, followed by the addition of the required amounts of DTDP (0.5M, pH 7) and vigorous stirring. An equimolar amount of DTDP, based on the —SH content of each ABSH polymer solution, was added. Gelation was observed visually by tilting the tube. To evaluate the ease of injection and uniformity of the gel within a capsular bag, a special mold, mimicking the natural pig lens, was used.

Figure 2:
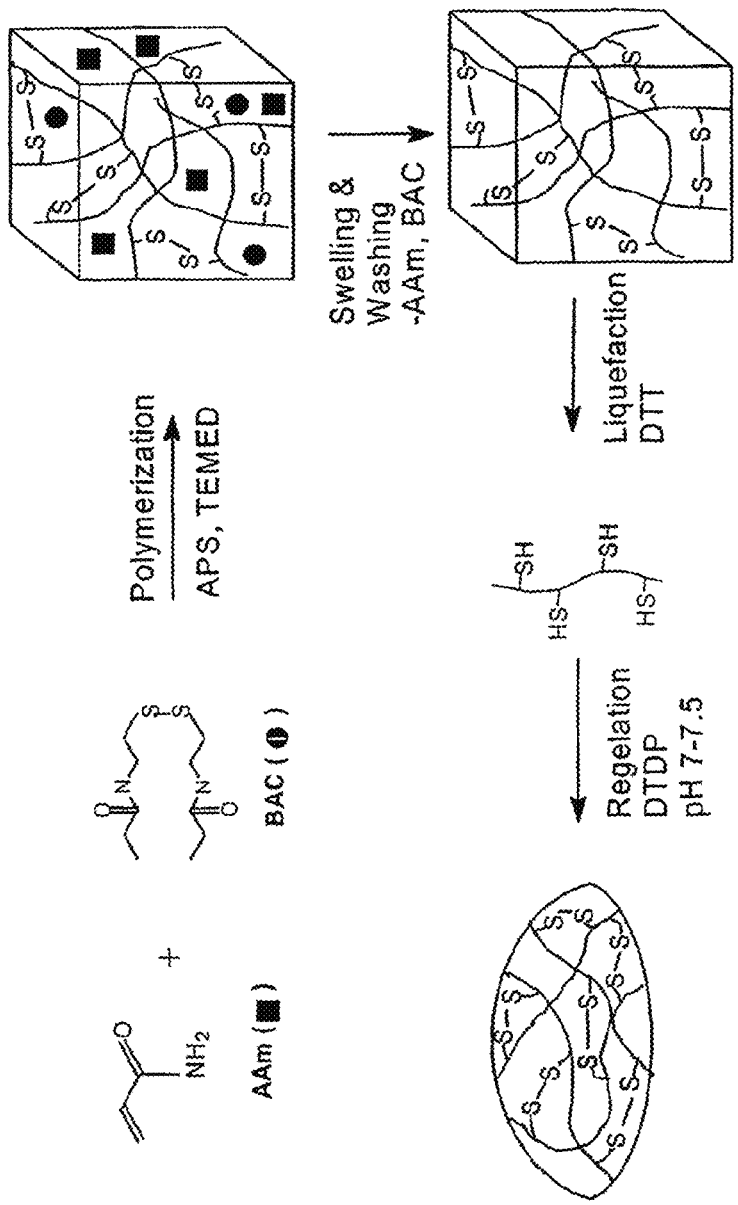
FIG. 2 shows the schematic of the preparation of the polyacrylamide/BAC reversible hydrogel system.

Preparation of cylindrical-shape gels was carried out using a Teflon mold. The static moduli of the re-gelled samples (as cylinders or thin discs) were determined from stress/strain experiments using a dynamic mechanical analyzer (Perkin Elmer DMA7e, Norwalk, Conn.) and the analyses were completed no less than one hour after the addition of DTDP. A static stress scan was performed from 0 to 25 mN at a rate of 5 mN/min at 25° C. Preparation of copolymeric hydrogels and their reduction and regelation from water-soluble copolymer are schematically shown in FIG. 2.

Endocapsular Gelation

Figure 3:
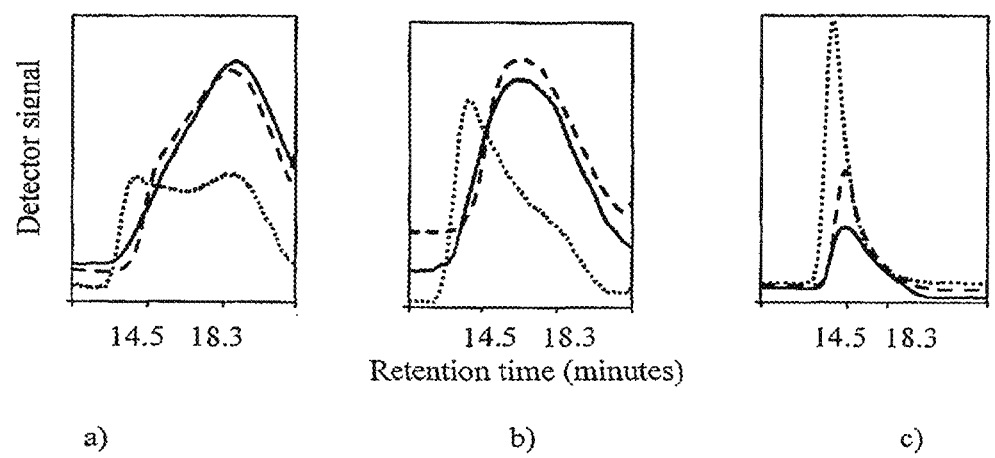
FIG. 3 shows the HPLC-GPC triple detector chromatograms of ABSH2 (continuous line), ABSH4 ( - - - ) and ABSH6 ( . . . ) polymers. Signals are from a) RI; b) viscosity; and c) light scattering detectors.

Copolymer solutions (% w/v) of 10.0 and 12.5% from ABSH2; of 5.0 and 7.5% from ABSH4; and of 2.0% from ABSH6, respectively, were evaluated for endocapsular gelation. Freshly enucleated pig eyes were purchased from a local abattoir shortly after slaughter. Typically, each eye was stabilized on a Styrofoam board; the cornea and iris were removed. A capsulotomy of from 1.0 to 1.2 mm diameter near the equator on the anterior capsular bag was performed using an Ellman Surgitron instrument (Edmonton, N.J.). The capsular bag was then evacuated using a Storz Phacoemulsification ultrasound instrument (Premiere, Bausch and Lomb, St. Louis, Mo.). DTDP was added to copolymer solution and mixed well just prior to injection. In a typical instance, 800 µL of 5% (w/v) solution of ABSH4 (pH adjusted to 7.4 using 10M NaOH) was placed, in a test tube and, 43 µL of DTDP (0.5 M, pH 7.0) was added and mixed thoroughly for 10 seconds in a vortex stirrer and drawn up in a syringe with a needle of 1.0 mm outer diameter, the tip of which was attached to a cone-shaped plastic microtip. The copolymer was injected carefully and quickly into the bottom of the capsular bag, which was thus filled without bubbles, and held closed for the next two to three minutes. The gelation usually occurred within three minutes. The surgical method of injection and re-gelation of the hydrogels are schematically represented in FIG. 3.

Results

Synthesis of poly(AAm-co-BAC) Hydrogels

Three different hydrogels of varying compositions were prepared from acrylamide and BAC at 2, 4, and 6 acrylic mole % of BAC with respect to acrylamide. As expected, increasing the BAC resulted in gels with better structural integrity. Gels having higher amount of BAC were slightly less transparent. ABSS2 did not form a stable gel but a viscous solution instead; however, stable gels were obtained at higher concentrations (>15%).

Synthesis and Characterization of ABSH Copolymers

The key step in obtaining water-soluble copolymers (ABSHs) from the crosslinked gels (ABSHs) involved the complete reduction of disulfide bonds (—S—S—) into thiol (—SH) groups, as shown in FIG. 2. Reduction of the gels by DTT resulted in almost complete reduction (as shown by the —SH content values in Table 1) of the disulfide bonds. Dissolution of the gels was significantly accelerated if nitrogen was bubbled through the solution. The —SH content of the water-soluble copolymers (ABSHs) is proportional to the BAC concentration used in the copolymerization, as shown in Table 1.

TABLE 1

| Gel Name | AAm/BAC (acrylic mole %) | —SH content ($\times 10^{-4}$ moles/g) | | Mean Mw ($\times 10^5$ D) |
|---|---|---|---|---|
| | | Calculated | Determined | |
| ABSS2 | 99/2 | 2.76 | 2.22 | 2.8 |
| ABSS4 | 98/4 | 5.44 | 5.37 | 4.28 |
| ABSS6 | 97/6 | 8.03 | 7.94 | 18.60 |

FIG. 3 shows the GPC traces of ABSH copolymers observed by the three detectors of the HPLC-GPC. Increasing the BAC content in the copolymerization increases the molecular weight and leads to broader molecular weight distribution, as shown in FIG. 3, trace a. The results of the weight-average molecular weight (Mw) of ABSH polymers are shown in Table 1.

Figure 4:
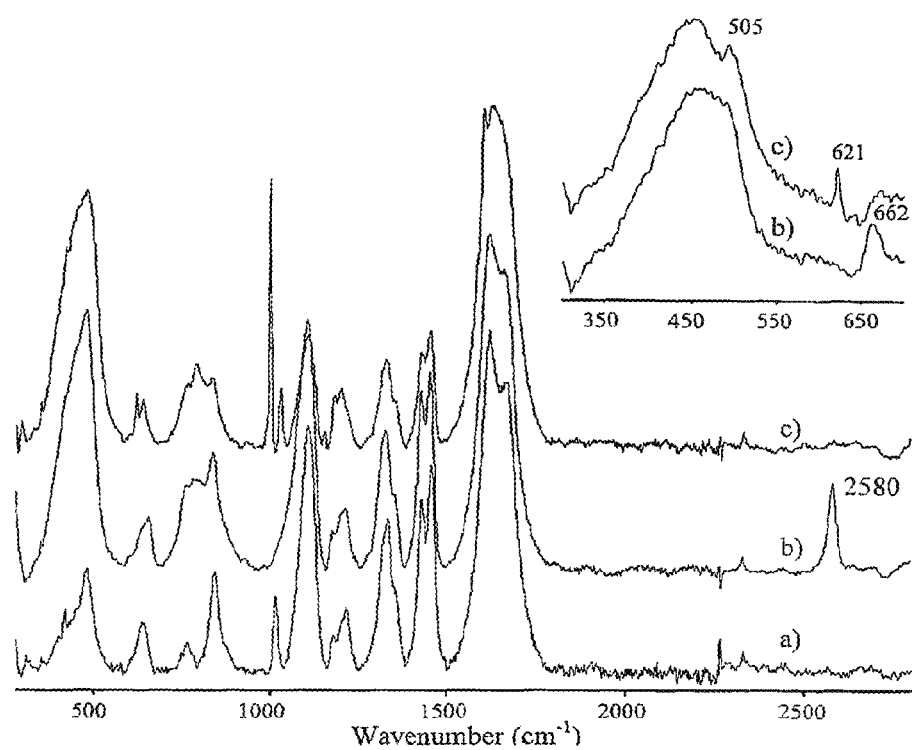
FIG. 4 shows the Raman spectra of a) 4% (w/v) aqueous solution of ABSH6 before gelation; b) 4% (w/v) aqueous solution of ABSH6 after gelation; and c) 5% (w/v) aqueous solution of polyacrylamide (prepared using the same experimental condition without BAC). Insert shows the expanded region of b) and c) after a) is subtracted.

Presence of thiol and its disappearance on regelation, with concurrent formation of disulfide (—S—S—) bonds, was confirmed by Raman spectroscopy. The Raman spectra of ABSH6 (4 w/v % aqueous solution) and its corresponding reformed gel, RABSS6 (the "R" indicating the reformed gel from ABSH6) are shown in FIG. 4. The characteristic absorption at 2580 cm$^{-1}$ corresponds to the —SH stretching vibration ($v_{SH}$), noted as trace b in FIG. 4, which disappeared completely upon gelling. The absorption corresponding to —S—S— stretch ($v_{S-S}$) usually appears at about 510 cm$^{-1}$, provided it does not overlap with any other vibration. Since the polymer is mostly polyacrylamide, it was difficult to observe the $v_{S-S}$ distinctly at $v_{S-S}$, noted as trace c in FIG. 4, because of interference from a broad, unsymmetrical —C—C— skeletal deformation peak of polyacrylamide centered at 485 cm$^{-1}$. This problem was resolved by subtracting the spectrum of polyacrylamide (trace a in FIG. 4, prepared using the same procedure, but without BAC) from the spectrum of the RABSS6. As shown in the insert of FIG. 2, the $v_{S-S}$ was clearly observed as a shoulder peak at 505 cm$^{-1}$.

In addition to the —SH and —S—S— vibrations, the peak positions of —C—S— stretch ($v_{C-S}$) from the —C—S—H moiety in ABSH6 and from —C—S—S—C— in RABSS6 were also observed distinctly at 662 cm$^{-1}$ and 621 cm$^{-1}$, respectively, after the subtraction of polyacrylamide spectrum, as shown in the insert of FIG. 4. In addition to the above characteristic absorptions, the other absorption peaks shown in FIG. 4 correspond to the Raman spectra of polyacrylamide (Gupta et al. Laser Raman spectroscopy of polyacrylamide. *J. Polym. Sci., Polym. Phys. Edit* 19:353-360, 1981).

Regelation and Mechanical Properties

Figure 5:
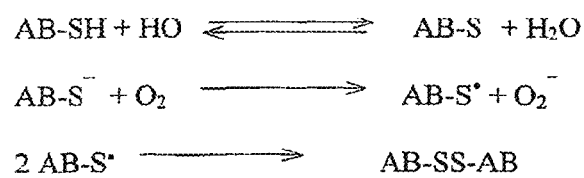
FIG. 5 shows oxidative regelation of thiol containing ABSH polymers via a) air oxidation at alkaline pH; and b) thiol disulfide exchange reaction.
Figure 5:
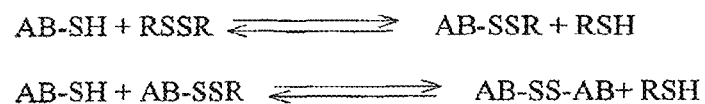

Regelation of ABSH polymers can be achieved by air oxidation of thiol or by thioldisulfide exchange reaction (FIG. 5). The reaction rate of one electron transfer from $ABS^-$ ion (from ABSH) to oxygen determines the rate of air oxidation of the thiol. This reaction rate increases with increasing pH. At pH 7.4, gelation usually occurred within 12 hours. Hisano et al. (Entrapment of islets into reversible disulfide hydrogels. *J Biomed Mater Res.* 40:115-123, 1998) reported that air oxidation took about six hours to form the gels at pH 8.8 for similar types of thiolated acrylamide polymers. Unlike air oxidation, the thioldisulfide exchange reaction resulted in gelation within a few minutes at pH between 7.0 and 7.5, which is closer to physiological pH. Since the gelation times were so short (all less than five minutes), we were able to carry out regelation experiments for several different concentrations of ABSH polymers. The concentrations of ABSH polymers and the static moduli of the re-gelled specimens are tabulated in Table 2. The modulus of gels formed at the same concentration increases with increasing molecular weight and —SH content. All of the reformed gels were transparent.

TABLE 2

| Gels from | Concentration from ABSH copolymers (% w/v) | | | | | | | |
|---|---|---|---|---|---|---|---|---|
| | 2 | 3 | 4 | 5 | 7.5 | 10 | 12.5 | 15 |
| | Modulus (KPa) | | | | | | | |
| ABSH2 | — | — | — | — | — | 0.333 | 0.800 | 0.786 |
| ABSH4 | — | — | — | 0.393 | 0.590 | 1.10 | — | — |
| ABSH6 | 0.385 | 0.467 | 0.556 | — | — | — | — | — |

In the present work, gelation occurred in less than 30 seconds for 15% solution of ABSH2, 10% solution of ABSH4, and 3 and 4% solutions of ABSH6. Because of the high viscosity and rapid gelation, however, endocapsular gelations were not attempted using these samples. Instead, air oxidation was the preferred technique. The lower concentrations, which are not included in Table 2, were not suitable for forming stable gels. Overall, the rate of gelation is a function of the oxidizing agent, pH, and light.

Endocapsular Gelation

Figure 6:
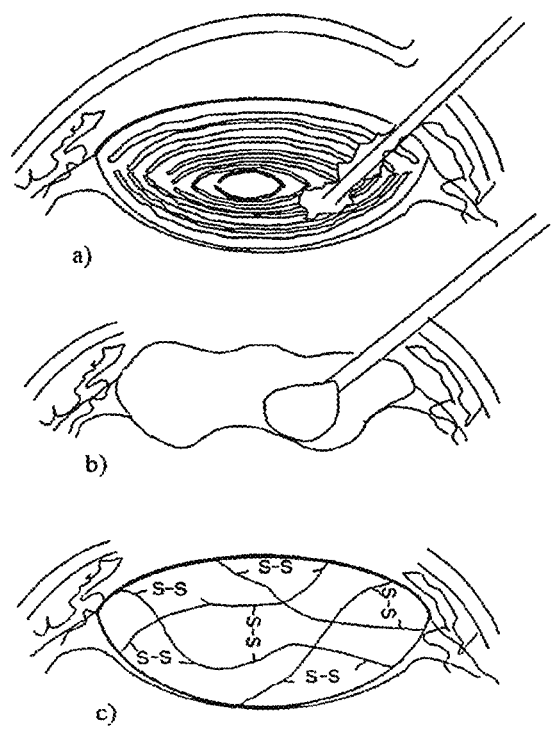
FIG. 6 shows a schematic of the surgical procedure for endocapsular hydrogel formation: a) perforation of the cornea and retraction of the iris, followed by the removal of the lens content; b) refilling the empty lens capsular bag with a solution of the reversible hydrogel material; and c) in situ regelation of the reversible hydrogel material.

The suitability of water-soluble copolymer solution (ABSHs) for endocapsular gelation was demonstrated in pre-evacuated porcine lens capsular bags. As stated earlier, very rapid re-gelation prevented testing of several polymer concentrations. Endocapsular gelation was performed using 10.0 and 12.5% solutions of freshly prepared ABSH2, 5.0 and 7.5% solutions of ABSH4, and 2.0% solution of ABSH6. In all these cases, regelation occurred within five minutes. Thanks to the high initial viscosity, which progressively, increased upon addition of DTDP, leakage during refilling did not occur. The surgical procedure of in-vitro refilling for endocapsular gelation is schematically represented in FIG. 6. Here, the cornea was perforated and the content of the lens was removed by phagofragmentation resulting in an empty capsular bag. The empty capsular bag was then refilled with the appropriate ABSH solution and regelled in situ.

Figure 7A:
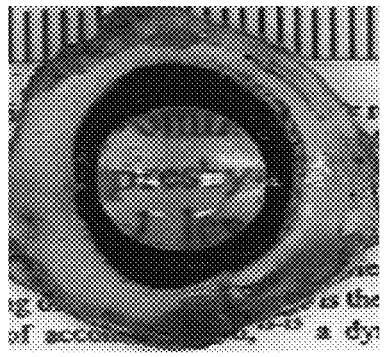
FIG. 7 shows re-gelled sample of 10 w/v % ABSH4 a) inside the porcine lens capsular bag; b) explanted from the lens capsular bag; and c) prepared in a mold.
Figure 7B:
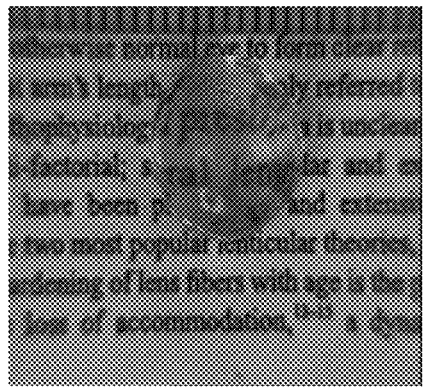
Figure 7C:
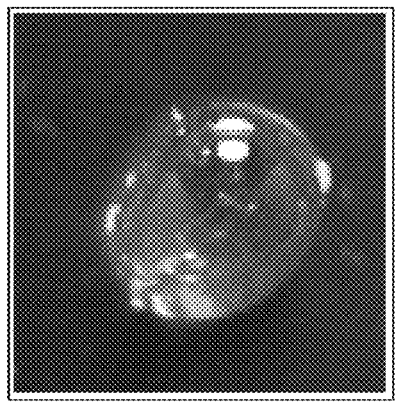

FIG. 7a shows a representative porcine eye sample where endocapsular gelation was carried out with a 10% (w/v) solution ABSH4. Objects viewed through the lens appeared clear and undistorted. FIG. 7b shows the re-gel lens explanted from the porcine lens capsular bag. Formation of uniformly transparent gels was also verified in molds shaped in the form of a lens (FIG. 7c).

Discussion

The primary aim of this work is to demonstrate the feasibility of using thiol containing copolymers as injectable precursors for in vivo chemical crosslinking under physiological conditions (ambient temperature, in the presence of oxygen, and at near-neutral pH). It is possible to form, in pre-evacuated capsular bags, optically clear gels whose modulus was approximately that of the youthful lens substance (~1000 Pa). The gelling chemistry uses the facile oxidation of pendant thiols to disulfide by slow air oxidation or the rapid exchange reaction mediated by suitable, non-toxic disulfide reagents. Such system is free of toxic monomers, does not involve exothermic reactions close to the living tissues, is leak-free, and has a rate of gelling that can be modulated by appropriate biocompatible accelerators and photons.

Here, polyacrylamide is used as a model scaffold or backbone structure and may be replaced by any polymer chain. Incorporating hydrophobic moieties can significantly enhance the solution property of the copolymer, i.e., viscosity and/or thixotropy. Additionally, thiols could be either pendant or at chain ends in a multi-armed polymer. The chemistry is also applicable to thiol-containing silicones, which have unusually high oxygen permeability. Because hydrophilic, water-swellable acrylates are usually biodegradable and not suitable for long-term use as vitreous substitutes or intraocular lens material, acrylamide derivatives are chosen for their generally greater hydrolytic stability. Another distinct advantage of this system is that the initial formation of a network outside the body facilitates the removal of heat as well as monomers and other toxic chemicals, problems that otherwise severely limit in vivo polymerization. The reduction of disulfide bonds in the hydrogel using DTT to obtain water-soluble ABSH copolymers is an important step that is influenced not only by the redox potential of the reducing agent, but also by concentration, time, pH, and nitrogen atmosphere. After considering these factors, it is found that using 10 molar excess of DTT and stirring under nitrogen to be most suitable approach for obtaining copolymers for endocapsular regelation. Use of acidified methanol (pH 3) during precipitation of the polymer was critical to maintaining the thiols in the reduced state during subsequent processing. Otherwise, the copolymers are only partly soluble. Upon drying, the samples were kept under reduced pressure until further use. As seen from the —SH content in Table 1, it is possible to reduce the disulfide bonds almost quantitatively. The gel can be reformed through either simple air oxidation or thiol-disulfide exchange reaction by adding DTDP. While the —SH content, concentration, and molecular weight of the copolymer influenced the regelation characteristics and moduli of the resultant gels, it is obvious from Table 2 that very high or low values of the above parameters render the material unsuitable for endocapsular gelation. In general, the modulus of the hydrogel increases with increasing —SH and copolymer concentration; and the hydrogel remains optically clear. Cystamine and 2-hydroxyethyldisulfide can also been used for regelation, but DTDP is less toxic than either of them.

In situ endocapsular hydrogel formation using reversible disulfide chemistry is a promising technique, not only for developing injectable intraocular lenses but also for use as vitreous substitutes, and topical medicaments. Unlike in situ polymerization and gelation, the reversible hydrogel system described here involves only in situ gelation, with no noticeable change in temperature. Because the copolymer is free of monomers and was injected at a concentration with a viscous consistency, toxicity from monomers and leakage is avoided. The time of regelation can be easily manipulated using DTDP, oxygen, pH, and/or photons.

Example 2

Acrylamide/BAC/N-phenylacrylamide Hydrogels (Hydrophobic Hydrogel)

Copolymerization of acrylamide (AAm), bisacryloylcystamine (BAC), and N-phenylacrylamide (NPA) was carried out at acrylic mole ratios of 94/4/2 at 5% (w/w) in 25% ethanol (25:75=ethanol:water v/v). Nitrogen was bubbled through the solution for about 30 minutes to remove any dissolved oxygen prior to the initiation of the polymerization. The reaction was initiated by adding 2.1% (w/w) of tetramethylethylenediamine and 0.4% (w/w) of ammonium persulfate and allowed to proceed for 15 hours at 25° C. Because of the limited solubility of BAC in water, aqueous ethanol was used as the solvent. The resulting gel was removed from the beaker, swelled in 500 mL of water for two days, crushed into small pieces and washed with distilled water. The copolymeric gel was labeled AB4N2SS indicating that it contained disulfide (—SS—) bonds by incorporating 4 acrylic mole % of BAC and 2 acrylic mole % of NPA.

The liquefaction of crushed gels (AB4N2SS) was achieved by the addition of dithiothreitol (DTT) (10 mol/mol of BAC used) to the crushed hydrogels. The reduction was carried out at pH 7.0 for 4 hours, while nitrogen was bubbled through the solution with stirring. After complete solubilization, the copolymer solution was acidified to pH 4 using 10% (v/v) HCl and precipitated in methanol (pH 4) with vigorous stirring. The precipitated —SH copolymer was filtered, dried under vacuum, and stored under reduced pressure at all times. The above obtained thiol containing water-soluble copolymer, from AB4N2SS was labeled AB4N2SH.

A 5% (w/v) solution of AB4N2SH was prepared in water ($N_2$ saturated) initially at pH ~4 and after the complete dissolution, the pH was adjusted to 7 using 7 μL of 5 M NaOH. Then, 162 μL of 0.5M DTDP (pH=7) was added to reform the hydrogel. The total volume of the composition was 3 ml. Similarly, 7%, 9%, and 11% (w/v) solutions of AB4N2SH were also prepared and used for the formation of hydrogels. The hydrogels were analyzed for their modulus values. The polymer solution (9, 11%) exhibited "honey-like" consistency, shear thinning when injected through the syringe, and almost instantaneously set within the pocine capsular bag as a physical gel without leaking. This physical gel was then transformed into a chemical gel.

TABLE 3

| Regelled hydrogels | Concentration of AB4N2SH polymers (% w/v) | | | |
|---|---|---|---|---|
| | 5 | 7 | 9 | 11 |
| | Static modulus (Pa) | | | |
| RAB4N2SS | 375 | 428 | 734 | 1008 |

Example 3

Hydrogels as Vitreous Substitute

The copolymer (AB4SH) was prepared from the hydrogel obtained by polymerizing acrylamide with 4 acrylic mole % of bisacryloylcystamine (BAC). The detailed experimental procedure was similar to those described in Example 1.

Figure 8A:
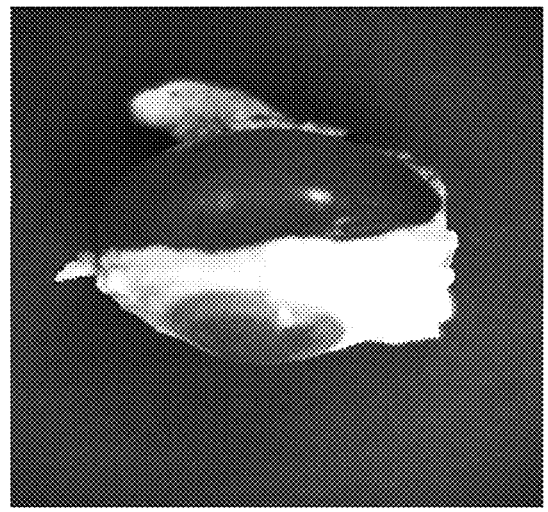
FIG. 8 shows a) vitreous substitute in human cadaver eyes seen after excision of the sclera, RPE, and retina; and b) eye dissected along the visual axis.
Figure 8B:
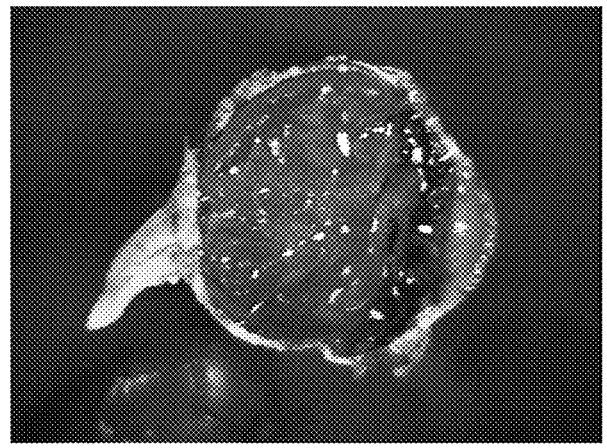

A 7% (w/v) solution AB4SH was prepared in water ($N_2$ saturated) initially at pH ~4 and after the complete dissolution, the pH was adjusted to 7 using 15 μL of 1 M NaOH. After which, 62 μL of 0.5M DTDP (pH=7) was added. The total volume of the composition was 1 ml and injected into pre-evacuated human cadaver eye vitreous cavity. The in-situ gel equilibrated with the residual water in the vitreous cavity thus making the final composition of the gel inside the cavity substantially less than 7% (FIG. 8). However, in general, gels containing higher percentage of BAC require lower concentration to gel and preferable as vitreous substitute.

In the current studies, acrylamide is employed as a monomer to be copolymerized with BAC, but other acrylamides or vinylmonomers can also be used. This technique of introducing pendant thiols into the polymer, along with appropriate choice of the primary polymer, can be used to design gels for specific end uses. Although much effort has been spent to develop biocompatible hydrogels, this reversible hydrogel system has not been previously investigated for in situ medical applications. Collectively, these observations indicate that this system is novel.

Example 4

Nanogels

Experimental Methods

Preparation of Copolymeric Hydrogels

Polyacrylamide/BAC hydrogel was prepared as above in Example 1. The polymer obtained was labeled as AB6SH. In the subsequent preparation of other types of copolymeric hydrogels, N-phenyl acrylamide, dimethylaminopropylmethacrylamide (DA), acrylic acid (AA) were additionally used to prepare the thiol copolymers with hydrophobic, positive and negative characteristics. The preparation of the copolymers and their composition are reported in Table 4.

TABLE 4

| | Feed composition of monomers | | | | | |
|---|---|---|---|---|---|---|
| Thiol polymers | AAm | BAC | NPA | AA | DA | Nanoparticle code |
| | Acrylic mole % (w/w) | | | | | |
| AB6SS | 94 | 6 | 4 | — | — | NP-AB6SS |
| AB4N4SH | 90 | 4 | 6 | — | — | NP-AB4N4SS |
| AB4N4AA3SH | 87 | 4 | 6 | 2 | — | NP-AB4N4AA2SS |
| AB4N4DA3SH | 87 | 4 | 6 | — | 2 | NP-AB4N4DA2SS |

Characterization of the Soluble Copolymer

The thiol (—SH) content present in the copolymers were determined using Ellman's analysis (Ellman, *Arch. Biochem. Biophys.*, 1959, 82:70-77). The molecular weight of the reduced polymer (ABSHs) was determined using a Viscotek HPLC-GPC system (Houston, Tex., USA) using dual column of G6000PWXL and G4000PWXL (Tosoh Biosep, Montgomery Ville, Pa., USA), connected in series. The mobile phase was 20 mM Bis-Tris buffer (pH 6.0, 0.1% sodium azide). Samples were prepared in water (pH 4, $N_2$ saturated) at a concentration of 0.5% (w/v). Polyethylene glycol standards (Viscotek, Houston, Tex., USA) of molecular weight (Mw) 1000 to 950,000 were used for calibration.

Preparation of Nanogels

A large volume of 0.1% w/v of thiol copolymer solution was prepared in water at pH 4. The pH of the solutions was adjusted to 7 using a small amount of 1M NaOH and bubbled with air for 3 days. Upon confirming the absence of the —SH by Ellman's analysis, the solution was concentrated to 25% w/w.

Preparation of Crystallin Solution

Porcine eye balls were obtained from the local abattoir and the lenses were dissected out. Decapsulated lenses were placed in buffer, (50 mM Tris, 50 mM NaCl, 1 mM EDTA, 1 mM DTT and 0.1% Na Azide) homogenized, and centrifuged at 12,000 RPM for 30 min. Approximately 1.2 g of the soluble fraction was loaded on a 5×90 cm Sephacryl S-300 Column (Pharmacia) and fractions were collected every 10 minutes with a flow rate of 1.3 mL/min. Absorbance was measured at 280 nm using an ISCO model UA-5 monitor. Fractions were pooled into their respective peaks of $\alpha$, $\beta_{high}$, $\beta_{low}$, and $\gamma$ crystallins and concentrated using an Amicon DC2 concentrator. The separated and concentrated materials were dialyzed against distilled water, lyophilized and stored at $-20°$ C. until used. The standard buffer used to re-suspend the samples was 20 mM Tris, 0.1% Na Azide, pH 7.6.

Rheological Experiments

A 4% w/w solution of $\beta_{high}$-crystalline (CBH) and NP-AB6SS were investigated for their viscoelastic behavior using the Vilastic-3 Rheometer (Vilastic Scientific, Austin, Tex.). Each sample was measured at a frequency of 2 Hz and at 22° C. in a cylindrical tube with a radius of 0.04953 cm and length of 6.278 cm. Measurements were performed over a range of shear rates from 2/sec to 900/sec for the fluid sample samples and 0.2/sec to 40/sec for the gel sample. For each sample measurements were performed on the first filling of the measurement tube and after a second filling of the measurement tube.

Determination of Refractive Index

The refractive indexes of the all the nanoparticles as well as crystallin solutions at different concentration were measured using Abbe refractometer (ATAGO's Abbe refractometer 1 T/4 T, Kirkland, Wash., USA) at 25° C.

Results and Discussion

Preparation and Characterization of Thiol Copolymers

Copolymerization of AAm and BAC resulted in hydrogel. The important step in obtaining the desired water-soluble copolymers (AB6SH) from the crosslinked gels (AB6SS) involves the complete reduction of all the disulfide bonds (—S—S—) in the gels into —SH groups as shown in FIG. 2. Similar to the preparation of AB6SH, other polymers were prepared using the different monomers mentioned in the Table 4.

Reduction of the gels by DTT resulted in almost complete reduction of the disulfide bonds as evidenced by the —SH determination. The Ellman's analysis showed —SH content to be $5.1 \times 10^{-4}$ and $7.9 \times 10^{-4}$ moles/g respectively for polymers containing BAC 4 and 6 acrylic mole %. The calculated values are $5.4 \times 10^{-4}$ and $8.0 \times 10^{-4}$ moles/g. The molecular weight distribution of the polymers showed broad distribution in general. The weight average molecular weights (Mw) were 9.1, 3.0, 4.3 and $1.75 \times 10^5$ Da for AB6SH, AB4N4SH, AB4N4AA2SH and AB4N4DA2SH respectively.

Preparation of Nanogels

Polymer containing pendent —SH groups (AB6SH) was used to prepare the nanoparticles (NP-AB6SS) through intramolecular crosslinking between —SH groups at very dilute concentrations. While very dilute concentrations favored the nanoparticle formation by intramolecular crosslinking only, the concentration studied (0.1% w/v) in this work still showed some intermolecularly formed nanoparticles. Ultra dilute concentration and control of the molecular weight distribution of the polymer will lead to the preparation of well defined nanoparticles. The nanoparticle formation by intramolecular crosslinking was represented in FIG. 9. Similarly, nanogels were prepared from other thiol polymers.

Refractive Index Nanogels and Lens Crystalline

Figure 10:
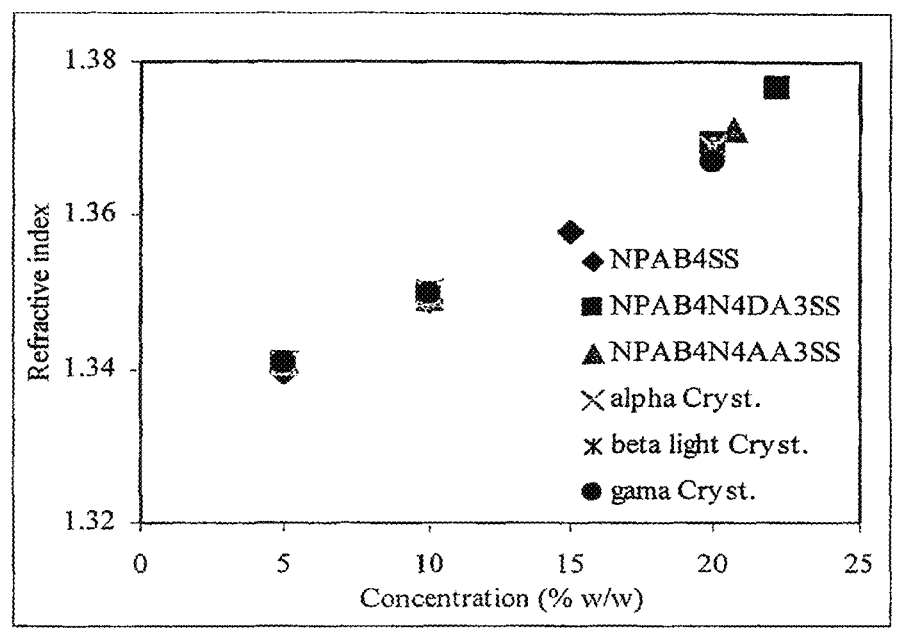
FIG. 10 shows refractive index values of disulfide containing nanogels and porcine lens crystalline proteins.

The refractive index (RI) values are presented in FIG. 10 for disulfide containing nanogels and protein molecules of lens crystalline. The RI values of the nanogels is similar to those of the crystalline.

Rheology Measurements of Nanogel and Crystalline

The viscoelastic characteristics of three polymeric samples were compared with that of $\beta_{high}$ crystalline (CBH) sample at same concentration (4% w/w). All the three samples, AB6SH, RAB6SH, NPAB6SS, were derived from the same polymer.

Figure 11:
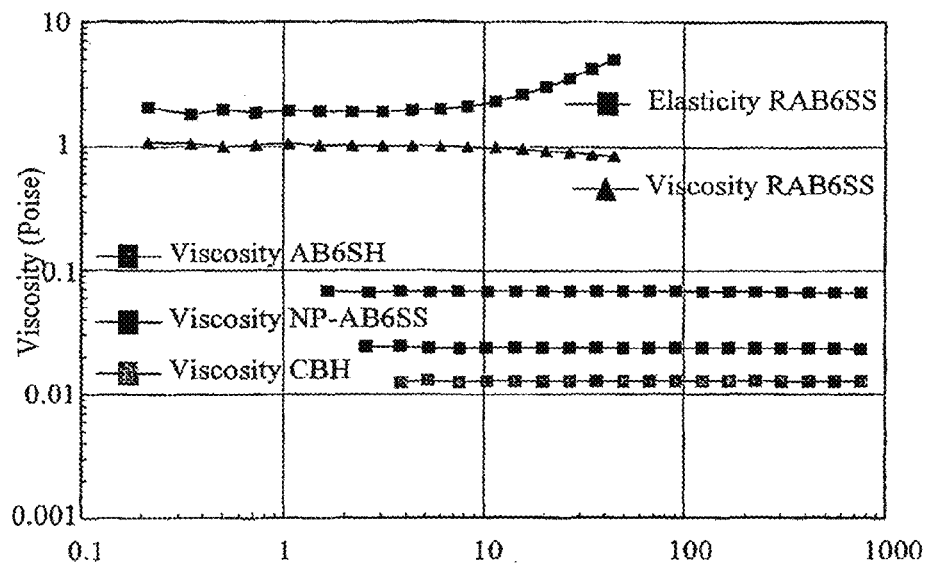
FIG. 11 shows viscoelastic characteristics of synthetic polymers and crystallins.

AB6SH is the copolymeric thiol obtained from the hydrogel prepared by polymerizing acrylamide and BAC at 94/6 acrylic mole ratio. RAB6SS is the re-gelled hydrogel sample from AB6SH polymer. NP-AB6SS is the nanogel sample prepared from the same AB6SH polymer as mentioned in the experimental section. The viscoelastic characteristics of nanogel (NP-AB6SS) showed very close resemblance to that of crystalline as observed in FIG. 11.

CONCLUSION

Thiol containing polyacrylamide copolymers were prepared from the hydrogels obtained by the polymerization of acrylamide and other monomers using disulfide containing crosslinking agent, bisacrylcystamine. The thiol polymers were used to prepare the nanogels through intramolecular crosslinking between thiol groups. Refractive index and viscosity of these nanogels were comparable to that of $\beta_{high}$ lens crystallins. The subtle difference in viscosity is attributed to the larger hydrodynamic volume of the nanogels and their polydispersity in size.

Example 5

Hydrogel Nanocomposite

Experimental Methods

Preparation of poly(AAm-co-BAC) Hydrogel and its Reduction

Polyacrylamide/BAC hydrogel was prepared as above in Example 1. The polymer obtained was labeled as AB4SH.

Characterization of the Soluble Copolymer

The thiol (—SH) content present in the copolymer (AB4SH) was determined using Ellman's analysis. The molecular weight of the reduced polymer (AB4SH) was determined using a Viscotek HPLC-GPC system (Houston, Tex., USA) using dual column of G6000PWXL and G4000PWXL (Tosoh Biosep, Montgomery Ville, Pa., USA), connected in series. The mobile phase was 20 mM Bis-Tris buffer (pH 6.0, 0.1% sodium azide). Samples were prepared in water (pH 4, $N_2$ saturated) at a concentration of 0.5% (w/v). Polyethylene glycol standards (Viscotek, Houston, Tex., USA) of molecular weight (Mw) 1000 to 950,000 were used for calibration.

Preparation of Nanoparticles a) From AB4SH thiol polymer: A large volume of 0.1% w/v of AB4SH polymer solution was prepared in water at pH 4. The pH of the solutions was adjusted to 7 using a small amount of 1M NaOH and bubbled with air for 3 days. Upon confirming the absence of the —SH by Ellman's analysis, the solution was concentrated to 25% w/w. The nanoparticle (solution) was labeled as NP-AB4SS.

b) From silica: Water soluble silica nanoparticles were prepared as reported by Mori et al. (*J. Am. Chem. Soc.*, 2003, 125:3712). The particle size was reported as ~3 nm diameter and was not characterized further here in this report. A stock solution of 65% w/w was prepared and used in the nanocomposites at different concentration.

c) From Bovine serum albumin (BSA): A 30% w/w solution of BSA in buffer (20 mM Bis-Tris, pH 6.0, 0.1% $NaN_3$) was prepared. This solution was used in the hydrogel nanocomposite materials at different concentrations.

Preparation of the Nanocomposites

Initially a 15% w/w solution of AB4SH in nitrogen saturated water was prepared at pH 4. This solution was mixed with the different nanoparticle solution at different concentration. The AB4SH concentration was kept constant at 5% w/w in all the compositions. The concentration of the nanoparticles was varied from 0 to 36% w/w as shown in the Table 5. The pH of composite was adjusted to ~7 using little of 1M NaOH just before the gelation. The nanocomposites were gelled using dithiopropionic acid (DTDP) in equimolar amount of thiol content of the AB4SH polymer. The composition and concentration of polymer and nanoparticles are shown in the Table 5.

Determination of Refractive Index and Moduli of Nanocomposites

The re-gelation of the composite materials was carried out in a cylindrical Teflon mold (10 mm dia and 5 mm height). The mechanical properties of these cyclindrical shape samples were determined by compression between parallel plates using a dynamic mechanical analyzer (DMA 7e, Perkin Elmer, Norwalk, Conn., USA). The refractive index of the re-gelled composite materials were determined using Abbe refractometer (ATAGO's Abbe refractometer 1 T/4 T, Kirkland, Wash., USA).

Results and Discussion

Preparation and Characterization of AB4SH Copolymers

Copolymerization of AAm and BAC resulted in hydrogel. The key step in obtaining the desired water-soluble copolymers (AB4SH) from the crosslinked gels (AB4SS) involves the complete reduction of all the disulfide bonds (—S—S—) in the gels into —SH groups as shown in FIG. 2.

Figure 9:
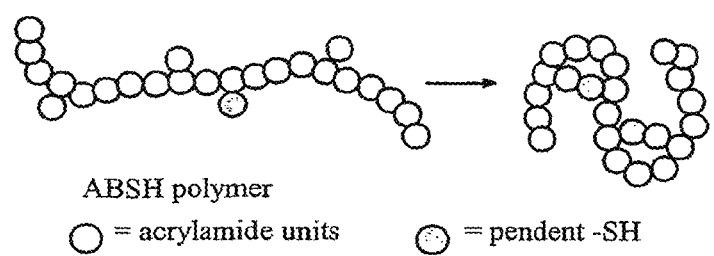
FIG. 9 is a schematic representation of the formation of a nanoparticle from ABSH polymer through intramolecular crosslinking between —SH groups.

Reduction of the gels by DTT resulted in almost complete reduction of the disulfide bonds as evidenced by the —SH determination. The Ellman's analysis showed —SH content to be $5.1 \times 10^{-4}$ moles/g. The calculated value is $5.4 \times 10^{-4}$ moles/g. The molecular weight distribution analysis of AB4SH showed a broad distribution with a polydispersity of 3.4 and weight average molecular weight (Mw) of $3.8 \times 10^5$ Da Preparation of Nanoparticles Polymer containing pendent —SH groups (AB4SH) was used to prepare the nanoparticles through intramolecular crosslinking between —SH groups at very dilute concentrations. While very dilute concentrations favored the nanoparticle formation by intramolecular crosslinking only, the concentration studied (0.1% w/v) in this work still showed some intermolecularly formed nanoparticles. Ultra dilute concentration and control of the molecular weight distribution of the polymer will lead to the preparation of well defined nanoparticles. The nanoparticle formation by intramolecular crosslinking is depicted in FIG. 9. The concentrated nanoparticle solution (25% w/v) was used in the preparation of nanocomposites at different concentrations.

Figure 12:
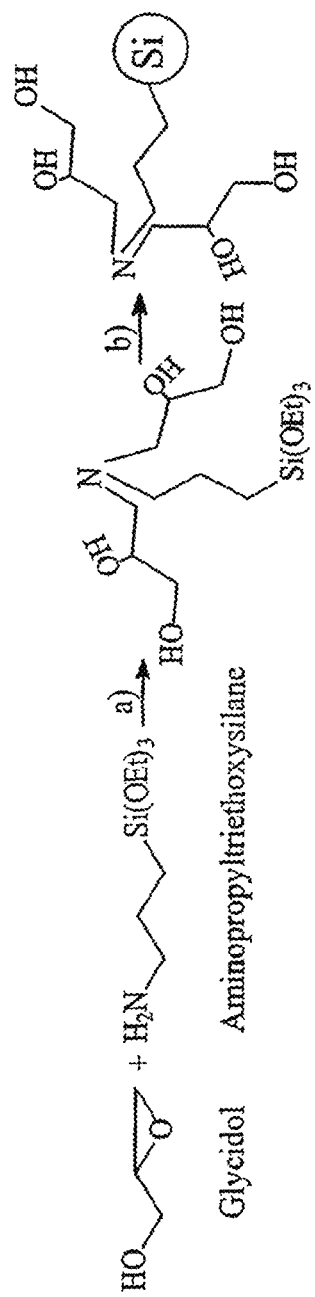
FIG. 12 is a schematic representation for preparation of silica nanoparticles through a) addition and b) acidic condensation reactions.

The silica nanoparticles were prepared by the addition reaction between glycidol and aminopropyltriethoxysilane followed by the acidic condensation of the addition product through sol-gel technique as reported by Mori et al. The particle size was reported as ~3 nm diameter. Because of higher hydroxyl group functionality of each silicon atom and very small size, these particles are well dispersed and behave like a dissolved molecule in water. A very high concentrated (65% w/w) solution was prepared and used in the nanocomposite hydrogel composition at different concentration. The preparation of the silica nanoparticles is shown in FIG. 12.

In order to compare and confirm the concept with a high concentrated solution of a biological molecule, BSA (30% w/w), was used as a nanoparticle solution in the nanocomposites.

Refractive Index and Moduli of Nanocomposites

The refractive index (RI) and moduli values are presented in the Table for all the nanocomposites. As the nanoparticle concentration increases the RI increases in all the composites. In the composite containing NP-AB4SS, the moduli values also increased. NP-AB4SS was prepared from AB4SH and was stable unless it was subjected to any reducing environment. But, when mixed with AB4SH in the composite, the thiol-disulfide exchange reaction occurred so that the disulfide bonds in the NP-AB4SS were broken and were incorporated into the AB4SH network upon regelation which resulted the higher modulus values. In the other two nanocomposites, neither BSA or silica nanoparticles react with the AB4SH polymer, instead there was a increase in the network defects and hence showed lower modulus values.

TABLE 5

| | | Nanoparticles from | | | | | | | |
|---|---|---|---|---|---|---|---|---|---|
| | | SS | | BSA | | | Silica | | |
| AB4SH (% w/w) | NP-AB4SS, (% w/w) | Modulus (kPa) | RI | BSA (% w/w) | Modulus (kPa) | RI | Silica (% w/w) | Modulus (kPa) | RI |
| 5 | 0 | 0.23 | 1.344 | 0 | 0.19 | 1.343 | 0 | 0.49 | 1.346 |
| 5 | 6 | 0.47 | 1.348 | 6 | 0.29 | 1.352 | 12 | 0.47 | 1.379 |
| 5 | 12 | 1.93 | 1.353 | 12 | 0.46 | 1.362 | 24 | 0.42 | 1.402 |
| 5 | 18 | 2.69 | 1.358 | 18 | 0.47 | 1.375 | 36 | 0.41 | 1.422 |
| 5 | — | — | — | 24 | 0.46 | 1.386 | — | — | — |

CONCLUSION

Polyacrylamide/BAC hydrogels were prepared and reduced to obtain water-soluble copolymer with pendant thiol (—SH) groups. The polymer was used to prepare the hydrogel nanocomposites with three different type of nanoparticle and regelled through the thiol-disulfide exchange reaction. Nanocomposite containing nanoparticles which did not react with the thiol polymer yielded hydrogel nanocomposite having high refractive index with lower moduli. It is envisioned that a system where the nanoparticle and the hydrogel are activated by different mechanisms may resolve this problem. For example, a system where the nanoparticle is light activated, while the hydrogel is pH activated, or vice versa, would eliminate thiol reactions between the hydrogel and the nanoparticle.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed:

1. An accommodating intraocular lens formed by in situ gelation of a hydrogel nanocomposite wherein said hydrogel nanocomposite comprises a hydrogel having nanoparticles dispersed therein and is formed from a reversible hydrogel, wherein said nanoparticles have diameters of less than 150 nm.

2. The accommodating intraocular lens of claim 1, wherein the nanoparticles are selected from the group consisting of nanogel, protein, silica, gold, silver, $TiO_2$, transition metals, ceramic, or combinations thereof.

3. The accommodating intraocular lens of claim 1, wherein the nanoparticles do not disperse or scatter visible light.

4. The accommodating intraocular lens of claim 1, wherein the nanoparticles have diameters between 3-20 nm.

5. The accommodating intraocular lens of claim 1, wherein the hydrogel further comprises a copolymer, wherein said copolymer is a hydrogel when in an oxidized state, and is a solution when in a reduced state.

6. The accommodating intraocular lens of claim 5, wherein the copolymer is produced by polymerization of a monomer with a crosslinker or a polymer derivatized to contain reversible crosslinking.

7. The accommodating intraocular lens of claim 6, wherein the monomer is selected from the group consisting of acrylamide, N-ornithine acrylamide, N-(2-hydroxypropyl)acrylamide, hydroxy-ethylacrylate, hydroxyethylmethacrylate, polyethyleneglycol acrylates, polyethyleneglycol methacrylates, N-vinyl pyrolidone, N-phenylacrylamide, dimethylaminopropyl methacrylamide, acrylic acid, benzylmethacrylamide, and methylthioethylacrylamide.

8. The accommodating intraocular lens of claim 6, wherein the crosslinker is selected from the group consisting of N,N'-bis(acryloyl)cystamine, vinyl groups, ally groups, cinnamates, acrylates, diacrylates, oligoacrylates, methacrylates, dimethacrylates, oligomethoacrylates, methylenebisacrylamide, methylenebismethacrylamide, esters of unsaturated mono- or polycarboxylic acids with polyols, trimethylolpropane triacrylate, allyl compounds, vinyl compounds, stilbene derivatives, azo derivatives, cinnamoyl derivatives, and combinations thereof.

9. The accommodating intraocular lens of claim 6, wherein the crosslinker is a disulfide linker.

10. The accommodating intraocular lens of claim 1, wherein the hydrogel can be reduced to form a solution.

11. The accommodating intraocular lens of claim 1, wherein the hydrogel can be reduced by the addition of a reducing agent.

12. The accommodating intraocular lens of claim 1, wherein the solution can be oxidized to reform the hydrogel.

13. The accommodating intraocular lens of claim 3, wherein the solution can be oxidized by atmospheric oxygen, or light and riboflavin.

14. The accommodating intraocular lens of claim 1, wherein the hydrogel comprises a copolymer, wherein said copolymer forms a hydrogel when exposed to light at a first wavelength, and forms a solution when exposed to light at a second wavelength.

15. The accommodating intraocular lens of claim 1, wherein the refractive index can be changed by changing the concentration of nanoparticles in the hydrogel.

16. The accommodating intraocular lens of claim 1, wherein the nanoparticles are selected from the group consisting of nanogels, proteins, silica, gold, silver, transition metals, $TiO_2$, ceramics, or combinations thereof.

* * * * *